United States Patent [19]

Hauser

[11] Patent Number: 5,089,181
[45] Date of Patent: Feb. 18, 1992

[54] METHOD OF DEHYDRATING VESICLE PREPARATIONS FOR LONG TERM STORAGE

[75] Inventor: Helmut O. Hauser, Zürich, Switzerland

[73] Assignee: Vestar, Inc., Pasadena, Calif.

[21] Appl. No.: 430,905

[22] Filed: Oct. 30, 1989

Related U.S. Application Data

[63] Continuation of Ser. No. 18,190, Feb. 23, 1987, abandoned.

[51] Int. Cl.$^5$ .................... A61K 9/127; A61K 9/133; B01J 13/02
[52] U.S. Cl. .................... 264/4.3; 264/4.1; 424/1.1; 424/7.1; 424/450; 436/829
[58] Field of Search ................. 264/4.1, 4.3; 424/450, 424/7.1; 436/829

[56] References Cited

U.S. PATENT DOCUMENTS

| | | | |
|---|---|---|---|
| 4,229,360 | 10/1980 | Schneider et al. | 264/4.3 X |
| 4,275,088 | 6/1981 | Hart et al. | 426/616 X |
| 4,370,349 | 1/1983 | Evans et al. | 514/785 |
| 4,508,703 | 4/1985 | Redziniak et al. | 424/450 |
| 4,515,736 | 5/1985 | Deamer | 264/4.3 |
| 4,830,858 | 5/1989 | Payne et al. | 424/450 |
| 4,895,719 | 1/1990 | Radhakrishnan | 424/45 |

FOREIGN PATENT DOCUMENTS

| | | | |
|---|---|---|---|
| 0140085 | 5/1985 | European Pat. Off. | |
| 55-122095 | 9/1980 | Japan | 424/450 |
| 0046921 | 3/1982 | Japan | 424/450 |

OTHER PUBLICATIONS

Hauser et al., "Stabilization of Small Unilamellar Phospholipid Vesicles During Spray-Drying", *Biochimica et Biophysica Acta*, vol. 897, No. 2, Feb. 26, 1987, pp. 331-334.

M. G. Coady "Development of Equipment for Lyophilization" in Proceedings of the 50th International Symposium on Freeze Drying of Biological Products, 1977, vol. 36, pp. 99-104, (S. Karger, Basel).

C. Judson King, "Applications of Freeze Drying to Food Products" in Freeze Drying and Advanced Food Technology, Chap. 21, 1975, Academic Press.

Mini Spray Dryer Buchi 190 Manual produced by Buchi Laboratory Techniques Ltd.

Table from Handbook of Chemistry, Handbook Publishers, Sandusky, 1956, p. 1667.

Masters, K., Spray Drying Handbook, 4th Edition, pp. 1-9, 299-342, 625-644 (1985).

Orndorff et al., Cryobiology, vol. 10 (6) 475-487 (1973).

Jennings, T., Practical Guide to Lyophilization, Stokes Penwalt Co. (1984).

Hauser et al., Biochim. Biophys. Acta 897, 331-334 (after Feb. 23, 1987).

Flamberg, D., Manufacturing Considerations in the Lyophilization of Parenteral Products in Pharmaceutical Manufacturing, Mar. 1986.

MacKenzie, A., Basic Principles of Freeze-Drying for Pharmaceuticals, Bulletin of the Parenteral Drug Assn., vol. 20 (4) 149-177 (1966).

*Primary Examiner*—Richard D. Lovering
*Attorney, Agent, or Firm*—Lyon & Lyon

[57] ABSTRACT

In the presence of a preserving additive, unilamellar phospholipid vesicle preparations are preserved during dehydration. Dehydration is effected by subjecting said preparations to a drying operations capable of causing flash evaporation.

17 Claims, 2 Drawing Sheets

FIG. 2A.
FIG. 2B
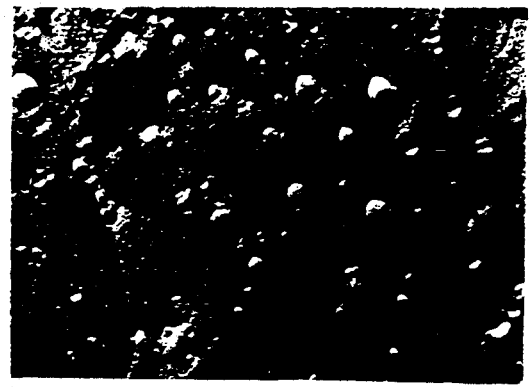
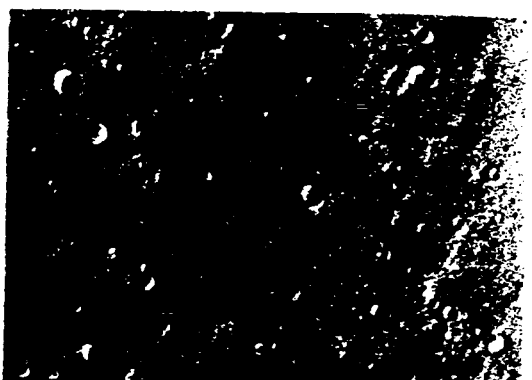
FIG. 2C
FIG. 2D
BAR = 100 nm

METHOD OF DEHYDRATING VESICLE PREPARATIONS FOR LONG TERM STORAGE

This is a continuation of co-pending application Ser. No. 18,190, filed on Feb. 23, 1987, now abandoned.

FIELD OF THE INVENTION

The invention described relates generally to the preservation of vesicles during dehydration procedures in the presence of a preserving additive whereby the integrity of the vesicle bilayer is maintained, aggregation or fusion is avoided, and there is no sacrifice of the utility of the vesicles.

One embodiment of the present invention is directed to vesicles preserved by spray-drying. Vesicles useful in the present invention include phospholipid vesicles inclusive of single unilamellar vesicles. The aforementioned preserved vesicles can be used, upon rehydration, for any purpose that vesicles not subjected to dehydration would be used.

BACKGROUND OF THE INVENTION

Liposomes are described quite widely in the literature and their structure is well known. Liposomes are unilamellar or multilamellar lipid vesicles which enclose a fluid space or spaces. The walls of the vesicles are formed by a bimolecular layer of one or more lipid components having polar heads and non-polar tails. In an aqueous (or polar) solution, the polar heads of one layer orient outwardly to extend into the surrounding medium, and the non-polar tail portions of the lipid associate with each other, thus providing a polar surface and non-polar core in the wall of the vesicle. Unilamellar liposomes have one such bimolecular layer, whereas multilamellar liposomes generally have a plurality of substantially concentric bimolecular layers.

A variety of methods for preparing liposomes are known, many of which have been described by Szoka and Papahadjopoulos, *Ann. Rev. Biophysics Bioeng.* 9: 467-508 (1980) and in *Liposome Technology*, Preparation of Liposomes, Vol I, Gregoriadis (Ed.), CRC Press, Inc. (1984). Also, several liposome encapsulation methods are disclosed in the patent literature, notably in U.S. Pat. No. 4,235,871, issued to Papahadjopoulos et al. on Nov. 25, 1980, and in U.S. Pat. No. 4,016,100, issued to Suzuki et al. on Apr. 5, 1977.

In order for liposomes to be useful in commercial settings, it is desirable to extend the shelf-life of liposomal preparations. Such preparations must have long enough shelf-lives to allow them to be easily manufactured, shipped and stored by intermediate and ultimate users under a variety of temperature conditions. With particular regard to the pharmaceutical industry, it is important to be able to store liposomal preparations for long periods of time without incurring substantial leakage of the incorporated drug.

Liposomal stability on storage is defined generally as the extent to which a given preparation retains both its original structure and size distribution and if applicable, its load of incorporated agent, whether therapeutic or diagnostic in nature. Instability can occur, for example, when vesicle size increases spontaneously upon standing as a result of fusion of colliding vesicles. The larger vesicles will exhibit drastically different pharmacokinetics in vivo because their size determines their clearance rates and tissue distribution; for instance, large liposomes are removed from the circulation more rapidly than smaller ones. In addition, liposomes in an aqueous liposome dispersion can aggregate and precipitate as a sediment. Although such sediments can usually be re-dispersed, the structure and size distribution of the original dispersion may be changed. Finally, another important factor with regard to instability is that incorporated substances of low molecular weight are likely to leak from stored liposomes. See generally G. Gregoriadis, *Liposomes for Drugs and Vaccines* in 3 Trends in Biotechnology, 235-241 (1985). If the content of the incorporated agent is small and/or the volume of the external aqueous medium is large, such leakage can represent a significant proportion of the total content of the agent in the liposomes.

Research directed to prolonging liposomal stability on storage has focused on liposome preservation in the form of lyophilization. Lyophilization refers to the process whereby a substance is prepared in dry form by rapid freezing and dehydration under high vacuum. Traditional wisdom dictates that phospholipid vesicles cannot be lyophilized successfully. Recent studies done by Drs. John and Lois Crowe at the University of California at Davis indicate that the disaccharide, trehalose, functions as a cryoprotectant during lyophilization and the studies conclude that optimal results are achieved when the cryoprotectant is located inside as well as outside the liposome. L. M. Crowe, et al., 1 Archives of Biochemistry and Physics 242 (1985). See also J. H. Crowe, L. M. Crowe, *Cryobiology*, 19, 317 (1982) *In Biological Membranes*, D. Chapman, Ed. (Academic Press, N.Y. 5, 57) in which it was reported that certain organisms such as nematodes, were able to survive dehydration in the presence of trehalose. Battelle Memorial Institute, Basel, has also disclosed the use of proteins and polysaccharides as liposome preservation agents during lyophilization, resulting in reported undamaged liposome levels of only approximately 70%. Schneider, et al., Process for the Dehydration of a Colloidal Dispersion of Liposomes, U.S. Pat. No. 4,229,360 (Oct. 21, 1980). Several other patents have been issued which disclose various methods to preserve liposomes utilizing lyophilization techniques. Evans, et al., Process for Preparing Freeze-Dried Liposome Compositions, U.S. Pat. No. 4,370,349 (Jan. 25, 1983); Weiner, et al., Storage-Stable Lipid Vesicles and Method of Preparation, U.S. Pat. No. 4,397,846 (Aug. 9, 1983); Vanlerberghe, et al., Storage Stability of Aqueous Dispersions of Spherules (Jan. 27, 1981). The stabilizing effect of sugars on sarcoplasmic reticulum subjected to freeze-drying and rehydration, and on microsomes and egg phosphatidylcholine SUV subjected to freeze-thawing have also previously been noted.

Lyophilization is an expensive procedure and would require considerable plant investment in order to produce dehydrated liposomal preparations on a commercial scale. Spray-drying and scrape surface drying (drum-drying) techniques, described generally in Hansen, U.S. Pat. No. 3,549,382 (Dec. 22, 1970), are less expensive to utilize commercially. Moreover, such techniques require the use of less energy than does the lyophilizing technique. Thin film evaporation constitutes an equivalent technology to spray-drying and scrape surface drying. Each of these three techniques is capable of causing flash evaporation, or rapid vaporization of a dispersion medium without damaging the integrity of the materials, in the present case liposomes, suspended in that medium. Such vaporization occurs in a temperature range of about 60° C. to about 150° C.

Recently unilamellar lipid vesicles have become important in several research areas dealing with membrane mediated processes such as membrane fusion, interfacial catalysis, energy conduction and conversion, drug delivery and targeting. There is hope that this kind of research will eventually lead to industrial applications of unilamellar lipid vesicles. In any practical application the questions of long-term storage and related to it vesicle and bilayer stability are important. It is well-known that aqueous dispersions of small unilamellar lipid vesicles (SUV) are thermodynamically unstable. For instance, SUV made of zwitterionic phosphatidylcholines tend to aggregate and/or fuse to large multilamellar lipid particles at room temperature. Furthermore, they undergo chemical degradation with time. The process of fusion of SUV is greatly accelerated when SUV are subjected to freeze-thawing or dehydration. It has been shown that SUV of egg phosphatidylcholine revert to large multilamellar structures upon freezing and thawing. G. Strauss and H. Hauser, Proc. Natl. Acad. Sci. USA 83, 2422 (1986), the disclosure of which is incorporated herein by reference. SUV are therefore an ideal system to test the stabilizing effect of various additives and to test dehydration by spray-drying or an equivalent technology.

SUMMARY OF THE INVENTION

The invention described herein is directed to the preservation of phospholipid vesicles through spray-drying and equivalent technologies in the presence of preserving additives.

The present invention contemplates drying methods capable of causing flash evaporation, or rapid vaporization of a dispersion medium. Spray drying and other equivalent technologies such as scrape surface drying or thin film evaporation can be used in the present invention.

In one embodiment, small unilamellar phospholipid vesicles are preserved by spray-drying in the presence of 5% -10% (0.15-0.3M) sucrose.

BRIEF DESCRIPTION OF THE DRAWINGS

FIGS. 2A-D show electron micrographs of sonicated mixed phospholipid dispersions of POPC/DOPS (mole ratio 7:3).

DETAILED DESCRIPTION

Abbreviations and Definitions

Figure 1:
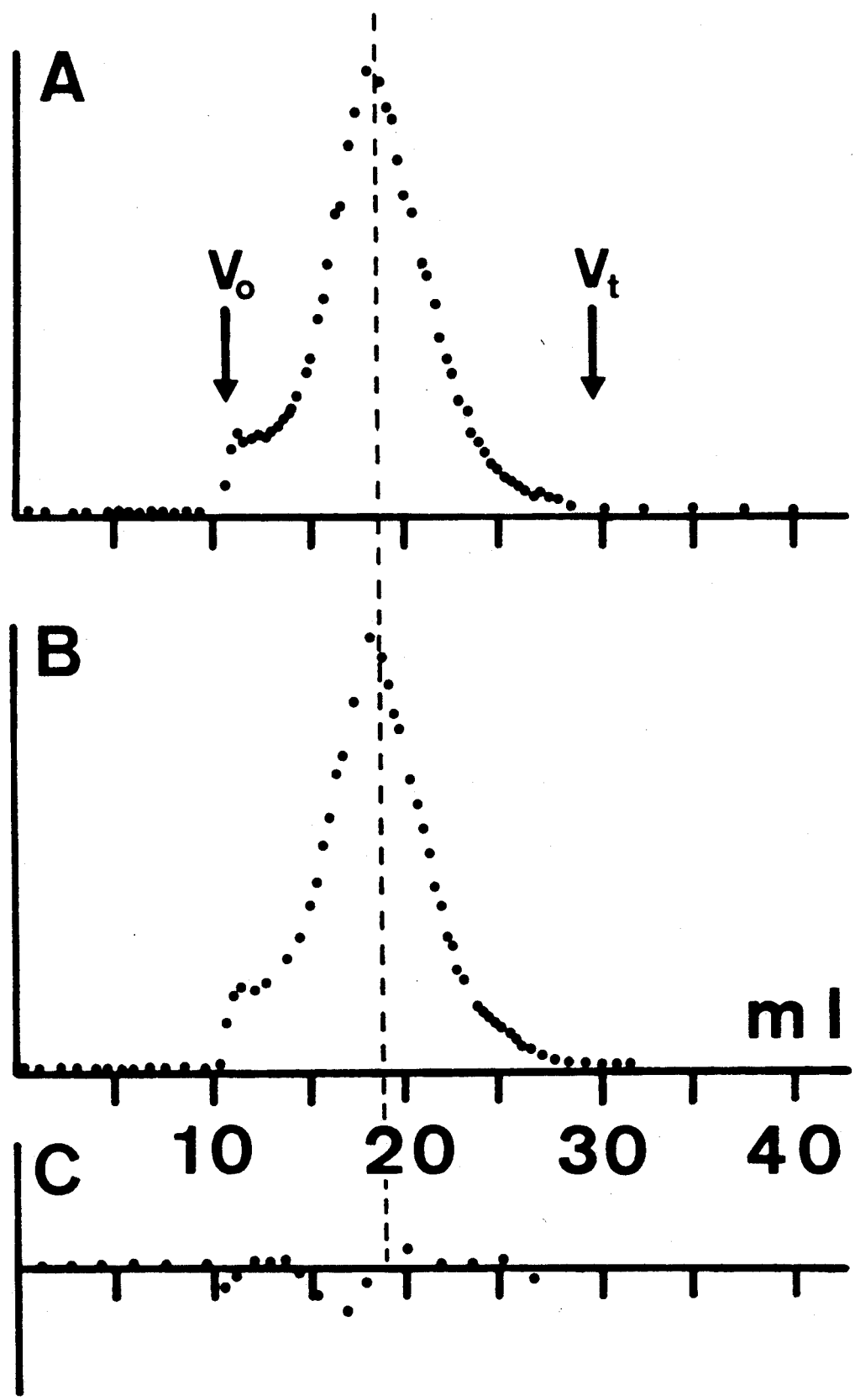
FIG. 1A graphically illustrates the typical elution profile of a sonicated phospholipid dispersion (1-palmitoyl-2-oleoyl-sn-phosphatidylcholine (POPC) /dioleoyl-sn-phosphatidylserine monosodium salt (DOPS), mole ratio 7:3 in buffer containing 10% (0.3M) sucrose.
FIGS. 1B graphically illustrates the elution profile of the same sonicated dispersion after subjecting it to spray-drying.
FIG. 1C graphically illustrates the difference profile when the above two elution profiles (1A and 1B) are superimposed.

SUV = small unilamellar vesicles
EPC = egg phosphatidylcholine
POPC = 1-palmitoyl-2-oleoyl-sn-phosphatidylcholine
DOPS = monosodium salt of dioleoyl-sn-phosphatidylserine
ESR = electron spin resonance
CAT 16 = 4-(N,N-dimethyl-N-hexadecyl) ammonium-2,2,6,6-tetramethylpiperidine-1-oxyl, iodide.

As used herein, "vesicle" refers to a micelle which is in a generally spherical form with an internal aqueous compartment, often obtained from a lipid which forms a bilayered membrane and is referred to as a "liposome." "Micelle" refers to a particle which results from aggregation of amphiphilic molecules. In this invention, preferred amphiphiles are biological lipids. Micelles are water-soluble aggregates of molecules with hydrophobic and hydrophilic portions (so-called amphiphilic molecules) which associate spontaneously.

Methods for forming vesicles are, by now, very well known in the art. Typically, they are prepared from a phospholipid, for example, 1-Palmitoyl-2-oleoyl-sn phosphatidylcholine and may include other materials such as neutral lipids, and also surface modifiers such as positively or negatively charged compounds. As used herein, "small unilamellar vesicle" refers to a vesicle with a simple bilayered spherical shell in the size range of less than about 2000A.

Suitable for use as a preserving additive in the present invention are any of a number of materials, including various carbohydrates, including specifically dextran and certain disaccharides such as sucrose and lactose, alcohols such as glycerol, mannitol and ethylene glycol, proteins such as ovoalbumin, and gum arabic. As used in the following examples, sucrose is illustrative of a suitable disaccharide. It will be understood by those skilled in the art that other preserving additives can be utilized within the confines of the present invention.

The vesicles of this invention are preferably in the form of small (less than 2000A) unilamellar phospholipid vesicles prepared by sonication as described by M. R. Mauk and R. C. Gamble, Anal. Bioc., 94, p. 302-307 (1979), or by microemulsification using the procedures described in a copending application by R. Gamble filed Jan. 31, 1985, now U.S. Pat. No. 4,753,788 and assigned to the same assignee as this application, both incorporated by reference herein.

Any of a variety of compounds can be enclosed in the internal aqueous compartment of the vesicles. Illustrative therapeutic agents include antibiotics, metabolic regulators, immune modulators, chemotherapeutic drugs, toxin antidotes, etc. By the same token, the vesicles may be loaded with a diagnostic radionuclide and fluorescent materials or other materials that are detectable in in vitro and in vivo applications.

In the preferred embodiment of this invention, the vesicles are preferably small unilamellar phospholipid vesicles which are subjected to spray-drying in the presence of preserving additives.

The present invention is most advantageous as it preserves the vesicles during the dehydration and subsequent rehydration. By "preservation", it is meant that average size and size distribution are not affected, that little or no fusion or aggregation is observed upon rehydration, that the vesicle bilayer integrity is maintained, and that there is no sacrifice of the utility of the vesicle.

MATERIALS AND METHODS

MATERIALS

Dioleoyl-phosphatidylserine (1,2-Dioleoyl-sn-glycero-3-phospho-L-serine [DOPS]) was synthesized according to Hermetter et al., (1982) Chemistry and Physics of Lipids, Vol. 30, p. 35, or was a gift of Ciba-Geigy (Basel, Switzerland). 1-Palmitoyl-2-oleoyl-sn-phosphatidylcholine (POPC), 1,2-palmitoyl-sn-phosphatidylcholine, 1,2-dioleoyl-sn-phosphatidylcholine were all synthesized according to Paltauf et al., (1971) Biochimica Biophysica Acta Vol. 249, p. 539. Egg phosphatidylcholine and ox brain phosphatidylserine were purchased from Lipid Products (Surrey, U.K.). The phospholipids used were 99% pure as determined by TLC. Sucrose, trehalose and glucose were obtained from Sigma Chemical Company (St. Louis, Mo.). Ascorbic acid was obtained from Fluka (Buchs, Switzerland). 4(N,N-dimethyl-N-hexadecyl)ammonium-2,2,6,6-tetramethylpiperidine-1,3-oxyl iodide (CAT 16) was purchased from Molecular Probes (Junction City, Oregon). $K_3Fe(CN)_6$ was obtained from Merck (Darmstadt, F.R.G.). $^3H(G)$—raffinose was a product of New England Nuclear (Boston, Mass.) while inulin [$C^{14}$]carboxylic acid (Mr =5200) was otained from Amersham International (Amersham, U.K.). Sephadex G-50 and Sepharose 4B were purchased from Pharmacia Fine Chemicals AB (Zurich, Switzerland).

METHODS

Vesicle Preparation

Sonicated phospholipid dispersions were prepared as described previously (Brunner et al., (1978), Journal of Biological Chemistry, Vol. 253, p. 7538). Briefly, 250 mg of phospholipid, e.g. POPC and DOPS, mole ratio 7:3) together with 1.7 mg CAT 16, if desirable, were dissolved in 10 ml $CHCl_3/CH_3OH = 2:1$ Vol/Vol), and the solution of phospholipid in organic solvent was dried by rotary evaporation. The film was dried in high vacuum ($<10^{-3}$ torr), and the phospholipid dispersion was made by suspending the dry phospholipid film in 5 ml 10 mM sodium phosphate buffer pH7 containing 5-10% (0.15-0.3M) sucrose (usually 10% sucrose was used). The phospholipid concentration was 50mg/ml unless otherwise stated, and the phospholipid to spin label (CAT 16) mole ratio was 100:1. The 5 ml dispersion was subjected to ultrasonication using a Branson B12 sonicator with a standard microtip. Sonication was carried out for 50 minutes in a glass vessel with a planar bottom, in an $N_2$ - atmosphere; the sample tube was immersed in ice water and the sonicator was used in the pulsed mode (50% duty cycle), i.e., alternating 30 second periods of sonication and cooling were applied. After sonication the sample was centrifuged at 5000 rpm for 10 minutes to remove Ti released from the tip of the sonicator. The sonicated phospholipid dispersion was diluted with buffer to a total volume of 50 ml(dilution factor = 10). 45 ml of the diluted sonicated dispersion were spray-dried using a Buchi spray-drying apparatus as described below. Any compound (material) to be entrapped in the internal aqueous cavity of the small unilamellar vesicles (SUV) formed by sonication, was added to the 10 mM phosphate buffer pH7 used to disperse the dry phospholipid film. In this way, $K_3Fe(CN)_6$ 3H-raffinose and $^{14}C$-inulin carboxylic acid were encapsulated. External $K_3Fe(CN)_6$, $^3H$-raffinose or $^{14}C$-inulin carboxylic acid were removed from SUV by gel filtration on Sephadex G-50 (medium). (Column dimension 19 cm×2 cm). Conditions of gel filtration: 3 ml phospholipid dispersion (80 mg/ml) were applied, the eluant was collected in a fraction collector, 15 drops =0.91 ml were collected per fraction, flow rate: 75 ml/hour. The eluant was analyzed for phosphate; fractions containing phospholipid were pooled and diluted to 50 ml. 45 ml of the diluted phospholipid dispersion were spray-dried in the Buchi spray-drying apparatus (see below).

METHODS

Spray-Drying

A Buchi spray-drying apparatus (Buchi Laboratory-Techniques, Flawil, Switzerland) was used. 45 ml of the diluted sonicated phospholipid dispersion were spray-dried (phospholipid concentration: ~5 mg/ml). The following instrumental parameters were used: pressure:4bar; spray-flow:520; aspirator:position 0; pump:position 1; heating rate:8.7-8.9; inlet temperature:140°±5° C.; outlet temperature:64° C.

After spray-drying both cyclones and all connections were rinsed with 20-30 ml $H_2O$ to rehydrate the dry phospholipid powder. The amount of water used to redisperse the dried phospholipid was adjusted to yield a phospholipid dispersion of similar concentration to that in the original dispersion (before spray-drying). The phospholipid was redispersed by gentle hand-shaking. The amount of phospholipid recovered after spray-drying varied between 50-75%. After spray-drying the purity of the lipid was checked by TLC. The procedure of spray-drying did not cause any detectable degradation of the phospholipids.

Gel Filtration of Phospholipid Dispersions On Calibrated Sepharose 4B Columns Gel filtration of sonicated phospholipid dispersions (consisting mainly of SUV) was carried out as described in detail by Schurtenberger and Hauser (1984), Biochimica Biophysica Acta, Vol. 778, p. 470. The calibration of the Sepharose 4B resin is also described in this reference.

Quasi-Elastic Light Scattering

Phospholipid vesicles were sized on a home-built instrument consisting of an argon-ion laser (Spectra Physics, Model 171, $\lambda=514.5$ nm), a temperature-controlled scattering cell holder, a digital autocorrelator (Malvern K 7023, 96 channels) and an on-line Nova 3 computer (Haller, H.R. (1980), Dissertation 6604, ETH Zurich).

Freeze-Fracture Electron Microcopy

Phospholipid dispersion samples for freeze-fracture electron microscopy were cryofixated, fractured and replicated as described by Hauser et al. (1983), Biochemistry 22: 4775 and references cited therein, the disclosures of which are incorporated herein by reference.

ESR - MEASUREMENT

In order to monitor the bilayer integrity and barrier properties an electron spin resonance test was used which was described in a previous publication (Strauss and Hauser, (1986), Proc. Natl. Acad. Sci. USA, vol 83, p. 2422, the disclosure of which is incorporated herein by reference). The spin label CAT 16 was incorporated in the phospholipid bilayer at a mole ratio of lipid to label of ~100:1. The free radical of this spin label is located in the polar group region of the bilayer. In sonicated dispersions consisting of SUV, the label is randomly distributed between the outer and inner layer of the bilayer, i.e., about 65-70% of the label is located on the external bilayer surface, the remainder is present on the inner bilayer surface. The phospholipid dispersion was cooled to 0° and 30 mM sodium ascorbate was added. Sodium ascorbate, which is a reducing agent impermeable to phospholipid bilayers at 0° C. will interact with the spin label located on the external bilayer surface. As a result 65-70% of the spin label intensity was quenched. Loss of the remaining "inner" ESR signal, which in intact membranes was -one-third of the total signal, is an indication that the bilayer becomes leaky for ascorbate.

ANALYTICAL METHODS

Phospholipids were quantified by determination of inorganic phosphorus using a slightly modified version of the method of Chen et al. (1956), Anal. Chem., Vol. 28, p. 1756. The concentration of $K_3 Fe(CN)_6$ was determined by absorption measurement at 420 nm. $^3$H-raffinose and inulin [$^{14}$C] carboxylic acid were quantified by radio counting in a Beckman LS 7500 liquid scintillation counter.

The following examples are presented to illustrate the invention, and are not intended to limit the scope thereof.

EXAMPLE 1

This example illustrates the ability of sucrose to stabilize SUV during spray-drying. A sonicated dispersion of POPC/DOPS, mole ratio 7:3 was prepared in 10mM phosphate buffer pH 7 containing 10% sucrose as described above. That the process of spray-drying did not change the morphology of the SUV dispersion (i.e. average vesicle size and size distribution) is illustrated in FIG. 1. The gel filtration pattern of SUV before spray-drying and that after spray-drying and redispersing the phospholipids are shown in FIGS. 1A and B, respectively. The elution patterns were very similar but not completely superimposable as evident from the difference pattern in FIG. 1C. The main peak of SUV (FIG. 1A and B) was eluted at an elution volume $V_e$, =19.3 ml corresponding to a Stokes radius of 125 A° (12.5 nm). The difference profile shown in FIG. 1C indicated that the spray-drying-rehydration cycle leads to some aggregation and/or fusion of SUV. A rough estimate of the extent of aggregation/fusion can be derived from the difference profile: not more than 10% of the phospholipid underwent aggregation/fusion. The conclusions derived from gel filtration on Sepharose 4B were supported by freeze-fracture electron microscopy. FIG. 2 demonstrates that sonicated dispersions of POPC-/DOPS (mole ratio =7:3) in phosphate buffer consisted of SUV of a diameter of 18-70 nm, both in the absence and presence of 10% sucrose (FIG. 2A and B, respectively). Subjecting these dispersions to spray-drying and redissolving the dry residue in $H_2O$ had little effect on the average vesicle size and size distribution provided sucrose was present in the buffer (FIG. 2D). The conclusions discussed above are further corroborated by sedimentation experiments. The sonicated POPC-/DOPS dispersion in phosphate buffer containing 10% sucrose was centrifuged at 12,000×g for 5 min. This centrifugation procedure has been shown to quantitatively pellet phospholipid liposomes present in unsonicated dispersions. The sonicated POPC/DOPS dispersion was centrifuged at 12,000×g for 5 min. before spray-drying and after spray-drying and redispersing the dry residue. In both instances, the pellet formed amounted to 2.5% of the total phospholipid dispersed. This experiment confirms that SUV are essentially retained during the process of spray-drying in the presence of 10% sucrose.

EXAMPLE 2

This is to illustrate that the same sonicated POPC-/DOPS dispersion as used in Example 1 undergoes aggregation and fusion during spray-drying if sucrose is absent. A sonicated dispersion of POPC/DOPS (mole ratio =7:3) in phosphate buffer pH7 (50 mg/ml) was prepared as described previously. Subjecting this dispersion, which did not contain any sugar in the buffer, to spray-drying and redispersing the dry residue in $H_2O$ led to drastic changes in the particle size. (FIG. 2C). Electron microscopy of freeze-fractured samples revealed the presence of large mainly unilamellar vesicles of diameter ~0.2 to 2 μm which contain smaller vesicles entrapped in their aqueous cavity. The electron micrograph shown in FIG. 2C closely resembles electron micrographs taken of unsonicated POPC/DOPS (mole ratio =7:3) dispersions. This result indicates that SUV undergo extensive aggregation and fusion during spray-drying in the absence of sucrose. This fusion process induced by spray-drying in the absence of sugar is also indicated by centrifugation. After spray-drying and redispersing the dry phospholipid in $H_2O$, the phospholipid dispersion was centrifuged at 12,000×g for 5 min: 97% of the phospholipid was pelleted under these conditions. This experiment demonstrates that a sonicated POPC/DOPS (mole ratio =7:3) dispersion after spray-drying and redispersing the dry phospholipid behaves like an unsonicated one.

EXAMPLE 3

Repeat of example 1. The sonicated phospholipid dispersion POPC/DOPS (mole ratio =7:3) in 10 mM phosphate buffer pH7 plus 10% sucrose was prepared as described previously. The concentration was 50 mg/ml before spray-drying. The average vesicle size and size distribution of the sonicated phospholipid dispersion was determined by gel filtration on Sepharose 4B before and after spray-drying. Before spray-drying, SUV eluted at $V_e$=19.2 ml corresponding to a Stokes radius of 12.5 nm. After spray and redispersing the dried phospholipid in $H_2O$, the main peak in the elution pattern was at $V_e$=18.6 ml. This somewhat lower value of the elution volume $V_e$ reflects a large average vesicle size, the Stokes radius thus derived was 13.6 nm.

EXAMPLE 4

In this example naturally occurring phospholipids were employed instead of the synthetic phospholipids used in examples 1-3. A sonicated phospholipid dispersion was made consisting of egg yolk phosphatidylcholine and ox brain phosphatidylserine (mole ratio =7:3). The mole ratio of the naturally occurring phospholipid mixture was the same as that of the synthetic phospholipid mixture used in examples 1-3. The sonicated phospholipid dispersion of egg phosphatidylcholine and ox brain phosphatidylserine in a 0.01M phosphate buffer, 10% sucrose was prepared in the same way as in examples 1-3. The sonicated phospholipid dispersion thus obtained was analyzed for the average vesicle size and size distribution using gel filtration on Sepharose 4B. The dispersion was chromatographed on Sepharose 4B before and after spray-drying. The results obtained were very similar to those discussed in examples 1 and 3. The conclusion is that the mixture of naturally occurring phospholipids behaved like that of the synthetic phospholipids.

EXAMPLE 5

This example shows that the vesicle size of SUV is essentially maintained during spray-drying, but the bilayer becomes permeable to ascorbate. A sonicated dispersion of POPC/DOPS (mole ratio =7:3) in 0.01 M phosphate buffer pH7 containing 10% sucrose was prepared as described previously. In this case the phospholipid bilayer was labeled with CAT 16. The signal height of the center line of the ESR spectrum was recorded (=100%). After addition of 10mM sodium ascorbate this signal height dropped to 33% because of the interaction of ascorbate with CAT located on the external bilayer surface. The dispersion was spray-dried and the dry phospholipid was redispersed in $H_2O$. After spray-drying no ESR signal was detected indicating that during spray-drying ascorbate had crossed the bilayer and reduced the remaining CAT molecules located on the internal bilayer surface.

EXAMPLE 6

Phospholipid SUV were prepared in exactly the same way as described in example 5. The sonicated phospholipid dispersion was involved. One half was made 10 mM in sodium ascorbate. The ESR spectrum was measured before and after the addition of Na+ ascorbate. The results discussed in example 5 were reproducible. The second half of the phospholipid dispersion was spray-dried and the dried phospholipid was redispersed in the appropriate amount of $H_2O$. The ESR spectrum was recorded and the signal height of the center line of the ESR spectrum was measured (=100%). To this dispersion 10 mM sodium ascorbate was added and the ESR spectrum recorded. Addition of ascorbate produced a reduction in signal height (=31%). This value of 31% is practically identical to that measured for the same dispersion before spray-drying. Before spray-drying the addition of 10 mM ascorbate to the lipid dispersion reduced the height of the center signal to 33%. The conclusions of this example are as follows:

(1) The fact that similar values were obtained for the signal height before and after spray-drying means that the vesicle size and size distribution cannot have changed significantly during spray-drying in the presence of 10% sucrose. This conclusion is consistent with conclusions derived from other methods, e.g. gel filtration on Sepharose 4B, Freeze-fracture electron microscopy and centrifugation.

(2) The bilayer becomes permeable to ascorbate during spray-drying. This is not too surprising considering that egg phosphatidylcholine bilayers have been shown to become permeable to Na+ ascorbate at room temperature. The experiment described in example 6 further suggests that any bilayer perturbation produced during spray-drying is reversible.

EXAMPLE 7

A sonicated POPC/DOPS dispersion in phosphate buffer plus 10% sucrose (mole ratio 7:3) is prepared as described previously. $^3H$—labeled raffinose is entrapped in the vesicle cavity and external [$^3H$,]- raffinose is removed by gel filtration on Sephadex G-50 as described previously. The lipid dispersion consisting of SUV with entrapped raffinose was chromatographed on Sepharose 4B before and after spray-drying. Before spray-drying it was found that 95% of the raffinose eluted together with the vesicle peak. After spray-drying 85% of the raffinose was eluted together with SUV. This experiment thus demonstrates that raffinose remains essentially entrapped during spray-drying at least to 90%.

EXAMPLE 8

The experiment described in example 7 was carried out in the same way except that [$^{14}C$]inulin carboxylic acid was encapsulated instead of raffinose. As expected from the results discussed above, example 8 showed that inulin encapsulated in the vesicle cavity remained encapsulated during spray-drying.

EXAMPLE 9

A sonicated phospholipid dispersion of POPC/DOPS (mole ratio=7:3) in 0.01M phosphate buffer pH 7 plus 10% (0.3M) sucrose was prepared as described in example 7. 0.1M $K_3Fe(CN)$, was added to the buffer in order to encapsulate $K_3Fe(CN)_6$. Externally present $K_3Fe(CN)_6$ was removed by gel filtration on Sephadex G-50. The experiment was then conducted as that described in example 7. After spray-drying the phospholipid dispersion of SUV containing $K_3Fe(CN)_6$, about 90% of the $K_3Fe(CN)_6$ was eluted with the SUV. This experiment allows the conclusion, that the bilayer barrier remains intact and ions do not penetrate the phospholipid bilayer during spray-drying.

From the foregoing examples, it is clear that the present invention provides for the preservation of vesicles during the dehydration techniques. Specifically, in the presence of 5-10% (0.15-0.3 M) sucrose, SUV made of phospholipids (POPC/DOPS, mole ratio 7:3) were preserved during spray-drying. In the absence of the sugar, spray-drying led to aggregation and fusion of SUV. In the case of SUV of charged phospholipids large unilamellar vesicles were formed. By preserving the vesicles in a dehydrated state, the vesicles can be stored for extended periods of time and aggregation or fusion of the vesicles is avoided without sacrifice of the utility of the vesicles or leakage of any enclosed material.

Although this invention has been described with reference to particular applications, the principles involved are susceptible of other applications which will be apparent to those skilled in the art. The invention is, therefore, to be limited only as indicated by the scope of the claims appended thereto.

I claim:

1. A method of dehydrating a liposome preparation, comprising spray drying liposomes suspended in an aqueous dispersion medium in the presence of a preserving additive at a temperature of 60° C. to 150° C., to produce a liposome preparation, which when reconstituted, maintains substantially the size, size distribution and integrity of the liposomes.

2. The method according to claim 1 wherein the liposomes are less than about 2000 A.

3. The method according to claim 1 wherein the liposomes are unilamellar.

4. The method according to claim 1 wherein the liposomes comprise phospholipids selected from the group consisting of phosphatidylcholines and phosphatidylserines.

5. The method according to claim 4 wherein said phosphatidylcholines are egg phosphatidylcholine, 1-palmitoyl-2-oleoyl-sn-phosphatidylcholine, 1,2-palmitoyl-sn-phosphatidylcholine and 1,2 dioleoyl-sn-phosphatidylcholine.

6. The method according to claim 4 wherein said phosphatidylserines are dioleoyl-sn-phosphatidylserine, 1,2 dioleoyl-sn-glycero-3-phospho-L-serine, and ox brain phosphatidylserine.

7. The method according to claim 1 wherein said preserving additive is selected from the group consisting of carbohydrates, alcohols, proteins and gum arabic.

8. The method according to claim 7 wherein said carbohydrate is dextran, a monosaccharide or a disaccharide.

9. The method according to claim 8 wherein said disaccharides are selected from the group consisting of sucrose, lactose and trehalose.

10. The method according to claim 8 wherein said monosaccharide is glucose.

11. The method according to claim 7 wherein said preserving additive is sucrose.

12. The method according to claim 11 wherein said sucrose is present in an amount from about 5% to about 10% sucrose.

13. The method according to claim 7 wherein said alcohols are selected from the group consisting of glycerol, mannitol and ethylene glycol.

14. The method according to claim 7 wherein said preserving additive is albumin or gum arabic.

15. The method according to claim 1 wherein the liposomes include therapeutic and/or diagnostic agents.

16. The method according to claim 15 wherein said therapeutic agents are selected from the group consisting of antibiotics, metabolic regulators, immune modulators, chemotherapeutics, and toxin antidotes.

17. The method according to claim 1 wherein the liposomes are subsequently reconstituted in an aqueous solution and upon reconstitution include therapeutic and/or diagnostic agents.

* * * * *